> United States Patent [19]

Tejera et al.

[11] 4,330,624
[45] May 18, 1982

[54] PROCESS FOR PRODUCING TUNICAMYCIN

[75] Inventors: Enrique Tejera, Caracas, Venezuela; Sara A. Currie, Roselle, N.J.; James E. Flor, Bridgewater, N.J.; Richard L. Monaghan, Somerset, N.J.

[73] Assignee: Merck & Co., Inc., Rahway, N.J.

[21] Appl. No.: 212,385

[22] Filed: Dec. 3, 1980

[51] Int. Cl.³ .............................................. C12P 19/60
[52] U.S. Cl. ........................................ 435/75; 435/897
[58] Field of Search ................................... 435/75, 87

[56] References Cited

U.S. PATENT DOCUMENTS 4,237,225 12/1980 Hamill .................................. 435/75

OTHER PUBLICATIONS

Takatsuki et al., J. Antibiotics, XXIV-4, 215–223, (1971).
Takatsuki et al., Agric. Biol. Chem, 41-11, 2307–2309, (1977).
Currie et al., Program and Abstracts, 11th International Congress of Chemotherapy and 19th Interscience Conference on Antimicrobial Agents and Chemotherapy, Abstract No. 508, 1–5 Oct. 1979.

Primary Examiner—Lionel M. Shapiro
Attorney, Agent, or Firm—Frank M. Mahon; Hesna J. Pfeiffer

[57] ABSTRACT

The antibiotic Tunicamycin is produced by fermenting a Tunicamycin-producing strain of Streptomyces (*Streptomyces griseus* ATCC 31591) under controlled conditions in a suitable nutrient medium and isolating the antibiotic so produced from the fermentation medium.

1 Claim, No Drawings

PROCESS FOR PRODUCING TUNICAMYCIN

The instant invention relates to a process for producing the antibiotic, Tunicamycin, which comprises growing a Tunicamycin-producing strain of Streptomyces in a suitable nutrient medium. More particularly, the instant invention relates to a process for producing the antibiotic, Tunicamycin, wherein *Streptomyces griseus* ATCC 31591 is grown in an aqueous nutrient medium comprising assimilable carbon and assimilable nitrogen sources under submerged aerobic conditions until substantial antibiotic activity is imparted to the medium and thereafter separating the antibiotic from the growth medium.

Tunicamycin is a well-known antibiotic which was first described in the literature by Takasuki et al. (Journal of Antibiotics, Vol. XXIV, No. 4, pgs. 215–223, April 1971). Although initially reported as a single compound, it was discovered subsequently that Tunicamycin actually is a complex in which the common structural units are uracil, N-acetyl glucosamine, a unique 11 carbon sugar and a fatty acid. (Takatsuki et al., Agric. Biol. Chem., Vol. 41, No. 11, pgs. 2307–2309, 1977). It is in the fatty acid moiety that the Tunicamycin complex differs. Thus it now is recognized that Tunicamycin is a mixture of homologus antibiotics containing four major components, each of which contains one mole of fatty acid with different carbon chain lengths. The structure of Tunicamycin and its four major components is shown below.

TUNICAMYCIN

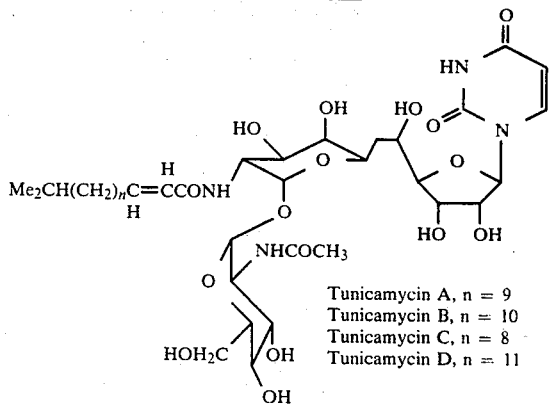

Tunicamycin A, n = 9
Tunicamycin B, n = 10
Tunicamycin C, n = 8
Tunicamycin D, n = 11

Tunicamycin is an antibiotic active against gram-positive bacteria, yeasts, fungi and plant and animal viruses. Further, since Tunicamycin acts by inhibiting the formation of lipid-linked intermediates in the biosynthesis of complex carbohydrates, it has become a valuable probe for molecular biologists.

The instant invention is based upon applicants discovery that the antibiotic, Tunicamycin, may be prepared by cultivating a heretofore unknown strain of *Streptomyces griseus*. The antibiotic is produced by growing said microorganism under controlled conditions in a fermentation medium followed by isolation of the antibiotic. The Tunicamycin complex so produced is identical to the Tunicamycin complex as reported in the literature cited above.

Based upon extensive taxonomic studies, *Streptomyces griseus* is identified as an actinomycete and has been designated MA-4729 in the culture collection of MERCK & CO., Inc., Rahway, N.J. A culture thereof has been placed on permanent deposit with the culture collection of the American Type Culture Collection, 12031 Parklawn Drive, Rockville, MD, 20852, and has been assigned accession No ATCC 31591.

The morphologic and cultural characteristics of *Streptomyces griseus* ATCC 31591 are set forth in the following table.

MORPHOLOGIC AND CULTURAL CHARACTERISTICS OF STREPTOMYCES GRISEUS ATCC 31591

(V = vegetative growth; A = aerial mycelium; SP = soluble pigment)

Morphology: Sporophores are branched, forming tufts, with spore chains straight to flexuous. Spores are spherical to oval (9.0 μ in diameter to $0.9 \times 1.2 \mu$) in chains of approximately 10–15 spores. Spore surface is smooth.

Oatmeal agar (ISP Medium 3)
  V: Reverse—brown, flat, spreading.
  A: Center—grayish-yellow, edge-drab tannish yellow (2db).
  SP: Slight browning of medium.
Czapek Dox agar (sucrose nitrate agar)
  V: Reverse—tan, flat, spreading.
  A: Powdery, tannish yellow (several shades but predominantly 2 db).
  SP: Light yellowish tan.
Egg albumin agar
  V: Reverse—grayish cream edged with tan.
  A: Tannish yellow with greenish cast (2 db).
  SP: Light tannish yellow.
Glycerol asparagine agar (ISP Medium 5)
  V: Reverse—cream edged with yellowish tan.
  A: Powdery, drab tannish-yellow (2 db).
  SP: None.
Inorganic salts-starch agar (ISP Medium 4)
  V: Reverse—tan edged with yellow-brown.
  A: Powdery, drab tannish yellow with greenish cast (2 db).
  SP: None.
Yeast extract-dextrose+ salts agar
  V: Reverse—tan edged with brown
  A: Drab tannish yellow (2 db).
  SP: Slight browning of medium.
Yeast extract-malt extract agar (ISP Medium 2)
  V: Reverse—tan edged with brown
  A: Drab, tannish yellow (2db).
  SP: Slight browning of medium.
Peptone-iron-yeast extract agar
  V: Tan
  A: None
  SP: None
Melanin: None
Carbon Utilization
  Pridham-Gottlieb basal medium +1% carbon source;
    + = growth; ± = growth poor to questionable;
    − = no growth as compared to negative control (no carbon source)
  Glucose    +
  Arabinose  ±
  Cellulose  −
  Fructose   +
  Inositol   ±
  Lactose    +
  Maltose    +
  Mannitol   +

Mannose +
Raffinose ±
Rhamnose ±
Sucrose ±
Xylose +

Temperature range (Yeast extract-dextrose+ salts agar)
°28° C. —Good growth with sporulation
°37° C. —Good growth with some sporulation
°50° C. —No growth.
Oxygen requirement (Stab culture in yeast extract-dextrose+salts agar)
Aerobic.
All readings taken after three weeks at 28° C. unless noted otherwise. pH of all media approximately neutral (6.8–7.2)
Color number designations taken from Color Harmony Manual, 1958, 4th Edition, Container Corporation of America, Chicago, Ill.

*Streptomyces griseus* characterized above differs from the description of the known Tunicamycin producer, *Streptomyces Lyosuperfieus*, in the color of spore-bearing mycelia (drab yellow), color of vegetative growth on certain media, especially potato, and lack of a soluble pigment on synthetic media. This strain also differs, either in sporophore structure or in color of spore-bearing mycelia, from the published descriptions of the *Streptomycetes* that produce compounds very similar to, and perhaps identical with, Tunicamycin (e.g. the compounds Mycospocidin, Streptovirudins of Series II, Antibiotic NM 19290 and Antibiotic 24010).

PREPARATION OF TUNICAMYCIN

Tunicamycin is produced according to the process of the instant invention during the aerobic fermentation of suitable aqueous nutrient media under controlled conditions via the inoculation with the organism *Streptomyces griseus* MA 4729 ATCC 31591. Such aqueous media contain sources of carbon, nitrogen and inorganic salts assimilable by the microorganism. The choice of media is not critical and the fermentation may be carried out in media containing suspended nutrient matter or predominantly clear media wherein the media is substantially free of suspended nutrient matter.

In general, carbohydrates such as sugars, for example, dextrose, glucose, arabinose, maltose, raffinose, xylose, mannitol and the like and starches such as grains, for example, oats, rye, corn starch, corn meal, potato and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, nutrient broth, yeast extract, yeast hydroylsates, primary yeast, soybean meal, cottonseed flour, hydroylsates of casein, corn steep liquor, distiller's solubles or tomato paste and the like. The sources of nitrogen, either alone or in combination, are used in amounts ranging from about 0.2% to 6% by weight of the aqueous medium.

The fermentation is carried out at temperatures ranging from about 20° C. to 37° C.; however, for optimum results it is preferable to conduct the fermentation at temperatures of from about 24° C. to 32° C. and desirably at 27°–28° C. The pH of the nutrient media suitable for growing the *Streptomyces griseus* MA 4729 ATCC 31591 culture and producing the antibiotic Tunicamycin should be in the range of from about 6.0 to 8.0.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days. At the end of the incubation period, the antibiotic activity is isolated from the fermentation broth by techniques hereinafter described.

The small fermentation may be conducted in a sterilized flask via a one-, two-, three- or four-stage seed development. The nutrient medium for the seed stage may be any suitable combination of carbon and nitrogen sources. The seed flask is shaken in a constant temperature chamber at about 28° C. until maximum growth is completed (usually one day) and some of the resulting growth is used to inoculate either a second stage seed or the production medium. Intermediate stage seed flasks, when used, are developed in essentially the same manner; that is, part of the contents of the flask are used to inoculate either the next stage seen medium or the production medium. The inoculated production flasks are shaken at a constant temperature for several days (usually 3 to 5 days) and at the end of the incubation period the antibiotic Tunicamycin is isolated.

For large scale work, it is preferable to conduct the fermentation in suitable tanks provided with an agitator and a means of aerating the fermentation medium according to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of several days as, for example from 3 to 5 days, while agitating and/or aerating the nutrient medium and maintaining the temperature at about 28° C.

A preferred process for preparing Tunicamycin is set forth below.

A lypholized tube of *Streptomyces griseus* MA 4729 ATCC 31591 is opened aseptically into a baffled 250 ml Erlenmeyer flask containing 50 ml of Medium A having the following composition:

| Medium A | |
|---|---|
| Soluble Starch | 10.0 g/l |
| Ardamine (Yeast Autolysate) | 5.0 g/l |
| NZ Amine E | 5.0 g/l |
| Beef Extract | 3.0 g/l |
| CaCO$_3$ | 0.5 g/l |
| MgSO$_4$ . 7H$_2$O | 0.05 g/l |
| Cerelose | 1.0 g/l |
| KH$_2$PO$_4$ | 0.182 g/l |
| Na$_2$HPO$_4$ | 0.190 g/l |
| Distilled Water | 1000 ml |
| pH 7.0–7.2 | |

The flask is shaken at 27°–28° C. on a 200 rpm shaker (2-inch throw) for one day. The growth from this seed-flask is used to inoculate a 250 ml Erlenmeyer flask containing 40 ml of Medium B using 2 ml/flask (5%) of inoculum.

| Medium B | | |
|---|---|---|
| Corn Meal | 20 | g |
| Distiller's Solubles | 10 | g |
| 4 S Soybean Meal | 15 | g |
| Na Citrate | 4 | g |
| $CaCl_2 \cdot 2 H_2O$ | 0.5 | g |
| $MgSO_4 \cdot 7 H_2O$ | 0.1 | g |
| $CoCl_2 \cdot 6 H_2O$ | 0.01 | g |
| $FeSO_4 \cdot H_2O$ | 0.01 | g |
| Polyglycol | 0.25% | by vol. |
| Distilled Water | 1000 | ml |
| pH 6.5 | | |

The flask containing Medium B is shaken at 27°–28° C. on a 220 rpm shaker (2-inch throw) for four days and submitted for extraction as described below.

ISOLATION OF TUNICAMYCIN

The whole broth obtained as described above (400 l) is filtered through diatomaceous earth and the mycelial cake is extracted twice with 60% aqueous acetone. The pooled extracts are evaporated in vacuo to remove the acetone. The pH of the concentrate is adjusted to 9 with 1 N aqueous sodium hydroxide and passed over a column of XAD-2 (Amberlite, Rohm & Haas Company, Philadelphia, Pa.) at a broth-to-resin ratio of 10:1 (v/v). The antibiotic activity is eluted with 85% aqueous acetone in one column volume. The eluate is evaporated to remove the acetone and the pH of the concentrate is adjusted to 3 with 1 N hydrochloric acid. The antibiotic activity is extracted into n-butanol twice and the combined extracts are evaporated to dryness. The residue is dissolved in methanol and chromatographed on a LH-20 (Pharmacia Fine Chemicals, Piscataway, N.J.) column in methanol. Active fractions are determined by silica gel thin layer chromatography developed in a 4:1:1 n-butanol-acetic acid-water system. The resulting chromatogram is visualized under uv (254 $\mu$m) light and is found to correlate with the bioautograph against *Saccharomyces cerevisiae*. Fractions thus selected are pooled and rechromatographed on a LH-20 column in n-butanol saturated with water. The eluate is evaporated and lyophilized to obtain purified Tunicamycin complex.

The subject matter which applicants regard as their invention is particularly pointed out and distinctly claimed as follows:

1. A method of producing the antibiotic, Tunicamycin, which comprises cultivating a Tunicamycin-producing strain of *Streptomyces griseus* ATCC 31591 in a fermentation broth containing assimilable sources of carbohydrates, nitrogen and inorganic salts under aerobic conditions until a substantial amount of Tunicamycin is produced in the fermentation broth and recovering the antibiotic.

* * * * *